US008399693B2

(12) United States Patent
Yalamanchili et al.

(10) Patent No.: US 8,399,693 B2
(45) Date of Patent: *Mar. 19, 2013

(54) PREPARATION OF AN ACTIVE INTERMEDIATE

(75) Inventors: Srikanth Yalamanchili, Bentonville, AR (US); Trevor Newbold, Salt Springs (CA); Sandra Mae Newbold, Salt Springs (CA)

(73) Assignee: Biobased Technologies LLC, Springdale, AR (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/403,214

(22) Filed: Feb. 23, 2012

(65) Prior Publication Data

US 2012/0178949 A1 Jul. 12, 2012

Related U.S. Application Data

(63) Continuation of application No. 13/066,096, filed on Apr. 6, 2011.

(60) Provisional application No. 61/341,926, filed on Apr. 7, 2010.

(51) Int. Cl.
C07C 51/16 (2006.01)

(52) U.S. Cl. ..................................................... 554/132

(58) Field of Classification Search .................. 554/132
See application file for complete search history.

(56) References Cited

U.S. PATENT DOCUMENTS

| 1,926,769 | A | 9/1933 | Hailwood et al. |
| 2,073,011 | A | 3/1937 | Hubbuch |
| 2,485,160 | A | 10/1949 | Niederhauser et al. |
| 2,752,376 | A | 6/1956 | Julian et al. |
| 3,169,139 | A | 2/1965 | D'Addieco |
| 4,749,517 | A | 6/1988 | Chwang et al. |
| 7,279,448 | B2 | 10/2007 | Erhan et al. |
| 7,893,287 | B2 | 2/2011 | Casper et al. |
| 2006/0041156 | A1 | 2/2006 | Casper et al. |
| 2011/0313124 | A1 | 12/2011 | Yalamanchili et al. |

FOREIGN PATENT DOCUMENTS

| DE | 4332292 | 3/1995 |
| WO | WO-2006-014521 | 2/2006 |

OTHER PUBLICATIONS

Friguelli et al. "One-Pot-Two Steps Synthesis of 1,2-Diol," *Synthetic Communications*, 1989, 19(11 & 12):1939-1943.
Luong, et al, "Direct Hydroxylation of Fats and Derivatives with a Hydrogen Peroxide Tungstic Acid System." *Journal of American Oil Chemists' Society*, 1967, 44:316-320.
Putilov et al. Chem. Abstr., 2003, 140-202144.

*Primary Examiner* — Deborah D Carr
(74) *Attorney, Agent, or Firm* — Wilson, Sonsini, Goodrich & Rosati

(57) ABSTRACT

A process for the preparation of an organic reactive intermediate that contains a combination of epoxy groups, hydroxy groups and unsaturated groups wherein the process can be utilized to control the amounts of each of the functional groups in the final product. The reactive intermediates are prepared from natural triglyceride plant and animal oils containing unsaturation.

22 Claims, 1 Drawing Sheet

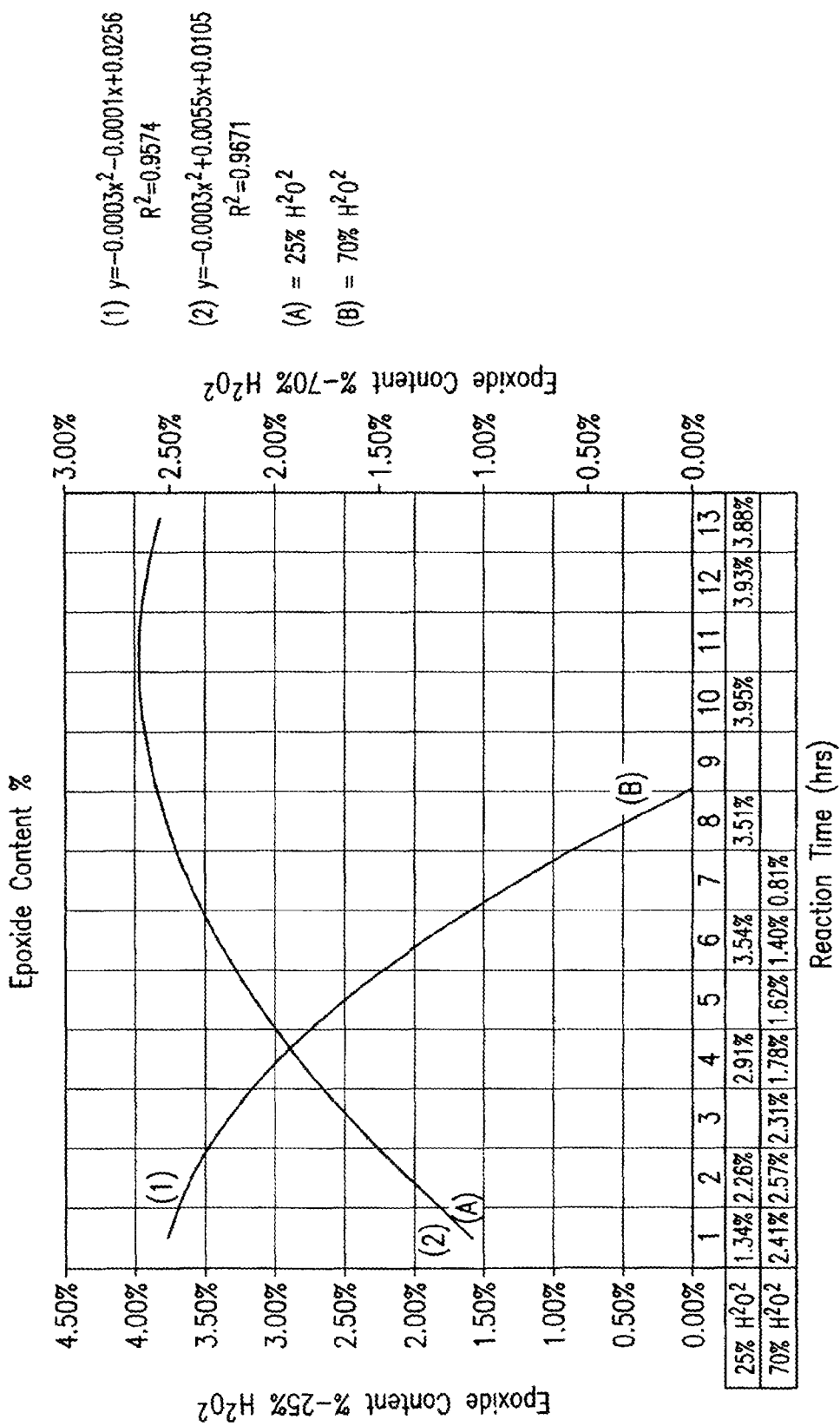

PREPARATION OF AN ACTIVE INTERMEDIATE

This application is a continuation of U.S. application Ser. No. 13/066,096, filed on Apr. 6, 2011, and claims priority from U.S. Provisional Application Ser. No. 61/341,926, filed Apr. 7, 2010.

BACKGROUND OF THE INVENTION

The contacting of a plant oil, carboxylic acid and hydrogen peroxide is well documented and can easily be found in the public domain. The focus of prior work in this area has been the preparation of epoxides and polyols from unsaturated triglycerides found commonly in a wide range of oil seeds.

These epoxides and polyols are polymerized with isocyanates to form polyurethanes, the isocyanate reacting with active epoxide and hydroxyl sites. The manufacture of these products using the materials outlined above requires heat, agitation, and owing to solubility limitations of the components, involves more than one liquid phase.

The desired end product of the resulting polyol is one that has active primary and secondary hydroxyl sites, with no interfering or competing functional groups. The desired end product of the resulting epoxide is a product that has no active, interfering or competing primary or secondary hydroxy sites. There has been very little work done on the preparation and use of hybrids comprised of active epoxide and hydroxyl sites in the same molecule and end use applications of the same.

This technology extends to the use of all mono and poly-unsaturated plant and animal derived triglycerides including those that have undergone transesterification to form esters, in what is commonly known as the biodiesel process.

*Camelina sativa* is a cruciferous oilseed plant. Also known as false flax or gold of pleasure, this natural oil source has been in use since Bronze and Iron Ages. The seeds contain 30-40% oil on a dry basis. The oil finds use in cooking and high omega-3 preparations such as salad dressing, mayonnaise, ice cream, pet foods, and, biodiesel. It has a fatty acid profile of 10% of saturated, 34% mono-unsaturated and 56% poly-unsaturated, with alpha-linolenic acid accounting for 35% of the oil.

The unsaturated fatty acid sites in camelina oil and all triglycerides are composed of carbon-carbon double bonds. These alkene sites are of particular interest in the preparation of functionalized plant oils for industrial use. This oil fits very well into the instant invention, in that, the oils that are preferred are those oils, or combination of oils that have up to $C_{22}$ carbon atoms.

These reactive alkene sites offer an opportunity to transform the camelina and other plant or animal derived oils into value added products suitable for use in the polyurethane, healthcare, energy, and other industries.

This invention is directed to a process for transforming these oils into reactive intermediates that contain moieties with a combination of alkenes, and either hydroxyl or epoxide, or a combination of hydroxyl and epoxide, reactive sites in the same product.

THE INVENTION

Thus, what is disclosed and claimed herein is a process for the preparation of organic reactive intermediates that contain a combination of epoxy groups, hydroxy groups and unsaturated alkene groups wherein the process can be utilized to control the amounts of each of the functional groups in the final product.

In one embodiment, the process comprises a multi-step preparation consisting of a first step of predetermining the concentrations of hydrogen peroxide and organic acid to be used in the process wherein the "organic acid" means that it is selected from group consisting of acetic acid, peracetic acid, formic acid, and performic acid.

Thereafter, predetermined amounts of plant and/or animal oils in any form, such as crude, refined, refined and deodorized, or, refined, bleached and deodorized (RBD), or a combination thereof consisting of plant oils and another consisting of plant oils and animal oils, having at least 1% by weight of unsaturation, based on the weight of the oils, or combinations thereof, is combined with the predetermined amounts of organic acid and hydrogen peroxide, in a reaction vessel. It is contemplated within the scope of this invention to use a mineral acid such as sulfuric acid during this step, as a catalyst.

The mixture is then heated to at least 45° C. under an inert atmosphere for a period of time of thirty (30) minutes to 168 hours, with stirring.

Thereafter, concentrating and deodorizing the product by sparging using a material selected from the group consisting of nitrogen, steam and air, at a temperature of 90° C. to 130° C. to provide a product having an acid number of 2.5 to 10 mg KOH/g and a hydroxyl number of up to about 230.

In a second embodiment, the process comprises a multi-step preparation consisting of a first step of predetermining the concentrations of hydrogen peroxide and organic acid to be used in the process.

Thereafter, a predetermined amount of fatty acid chains cleaved from animal and plant triglyceride backbone, or the methyl esters derived from the same, that are by-products of the manufacture of biodiesel as starting materials, are added. All grades of unsaturated biodiesel (methyl or ethyl esters) serve as suitable starting raw material for this process. These materials must also have at least 1% by weight of unsaturation, based on the weight of the biodiesel raw material. These materials are combined with the predetermined amounts of organic acid and hydrogen peroxide, in a reaction vessel. As set forth above, a mineral acid such as sulfuric acid can be used as a catalyst during this step.

The mixture is then heated to at least 45° C. under an inert atmosphere for a period of time of thirty (30) minutes to 168 hours, with stirring.

Finally, the product is concentrated and deodorized by sparging using a material selected from the group consisting of nitrogen, steam and air at a temperature of 90° C. to 130° C. to provide a product having an acid number of up to 10 mg KOH/g.

The process is designed to give triglyceride hybrids having alkene, epoxide and hydroxyl content at variable levels. These products are functionally different from prior art materials in structure and chemical reactions when employed in industrial applications due to the reaction characteristics of the functional groups present.

This process provides intermediates having high hydroxyl numbers (up to 230) with low color such as Gardner Color number of seven (7) or less with the preferred level being at a Gardner Color number of five (5) or less and a most preferred product having a Gardner Color number of three (3) or less.

This process also provides intermediates having high acid number that is an acid number of 2.5 to 10 mg KOH/g.

BRIEF DESCRIPTION OF THE DRAWINGS

FIG. 1 is a graph that can be used to determine the concentrations and ratios of the various components for the reaction using 25% or 70% w/w hydrogen peroxide.

DETAILED DESCRIPTION OF THE INVENTION

The invention described and disclosed herein deals with a process for the preparation of organic reactive intermediates that contain a combination of unsaturated groups, and epoxy groups or hydroxy groups, or a combination of epoxy groups and hydroxy groups. The organic reactive intermediates are derived from natural triglyceride plant and/or animal oils or combinations having at least one percent (1%) by weight of unsaturation, based on the weight of the natural triglyceride oils.

Table I is a table listing many of the oils that can be used although this invention is not limited by such disclosure.

TABLE I

Triglycerides and their Iodine Values

| Oil | Iodine Value |
| --- | --- |
| Mutton tallow | 40 |
| Beef tallow | 50 |
| Palm oil | 54 |
| Olive oil | 81 |
| Castor oil | 85 |
| Peanut oil | 93 |
| Rapeseed oil | 98 |
| Cotton seed oil | 105 |
| Sunflower oil | 125 |
| Soybean oil | 130 |
| Tung oil | 168 |
| Linseed oil | 190 |
| Camelina oil | 150 |
| Sardine oil | 185 |

Preferred are plant oils, camelina, canola, jatropha, soy, and animal oils, sardine, herring, and beef tallow.

Especially preferred are linseed, canola, soy, jatropha, camelina and sardine oils. Camelina oil has an approximate iodine number of about 150 as opposed to soy oil at about 130. Iodine number is a reflection of the level of unsaturation (carbon-carbon double bonds) present in a triglyceride. Approximately 90% of the camelina triglyceride is unsaturated. The plant and animal oils useful herein can be crude, refined, refined and deodorized or, refined, bleached and deodorized (RBD) types of plant and animal oils.

Triglycerides can also be selected from non-food sources and preferably those with natural levels of alkenes, epoxides, alcohols and carboxylic acids, or any combinations of these, or other functional groups.

Of further interest in this invention are those oilseeds that have been genetically modified to enhance the seed's epoxide and/or hydroxy content. Further, of interest are those oil seeds that meet the above criteria but are considered low input industrial oil seed crops that do not compete with food crops. Preferred examples of these materials are vernonia anthelmintica seed oil, chrysanthemum coronarium seed oil, camelina sativa seed oil, and ricinus communis seed oil.

For purposes of this invention, the natural oils and esters must have at least one percent (1%) of unsaturation. The oils are combined with a predetermined amount of hydrogen peroxide and organic acid which converts a portion of the unsaturated carbon-carbon double bonds into epoxy groups, and then a portion of the epoxy groups into hydroxy groups.

The amount of conversion of the above-mentioned functional groups is dependent on the amounts and ratios of the hydrogen peroxide and acid, and on the time and temperature of reaction.

With reference to FIG. 1, there is shown a graph that can be used to determine the concentrations and ratios of the various components for the reaction in order to end up with a product having the approximate amounts of functional groups that are desired.

For example,
From FIG. 1:

Triglyceride (Camelina Oil) Reaction Profile

Example 1

If the desired product requires a hydroxyl number of 115 and epoxide content of 2.4%, the following raw materials are required.

Hydrogen Peroxide (50% w/w): 287 g
  1. Acetic Acid, glacial: 253 g
  2. Camelina oil (Refined), Iodine number 150: 1045 g
  3. Reaction time: 8 Hrs Example 2

If the desired product requires a hydroxyl number of 167 and epoxide content of 0.5%, the following raw materials are required.
  1. Hydrogen Peroxide (70% w/w): 205 g
  2. Acetic Acid, glacial: 253 g
  3. Camelina oil (Refined), Iodine number 150: 1045 g
  4. Reaction time: 13 hrs Example 3

If the desired product requires a hydroxyl number of 44 and epoxide content of 4.0%, the following raw materials are required.
  1. Hydrogen Peroxide (25% w/w): 487 g
  2. Acetic Acid, glacial: 215 g
  3. Camelina oil (Refined), Iodine number 150: 888 g
  4. Reaction time: 21 hrs The preferred order of addition is oil, followed by the simultaneous addition of acid and hydrogen peroxide. A second option is oil followed by acid and finally hydrogen peroxide. The preferred option is the simultaneous addition of oil, acid and hydrogen peroxide. In the first two cases the acid and oxidant are metered in. In the preferred option, the oil, acid and hydrogen peroxide are all metered in.

The concentration and deodorization steps are the same as described earlier for all three (3) examples given.

The reaction of the unsaturated functional plant and animal oils to a portion of epoxy groups and a portion of hydroxy groups is enhanced by the use of acetic or formic acid containing water and these components are put into the reaction at the very beginning of the process. The formic acid, if substituted for acetic acid, speeds up the epoxide ring formation and also accelerates the epoxide ring opening to form hydroxy groups. Alternately, a mineral acid such as sulfuric acid can be used as a catalyst to accelerate the reaction.

It has been determined that this reaction can be carried out at or near atmospheric pressure. Also, it is contemplated within the scope of this invention to carry out this reaction under an inert blanket of gas, such as nitrogen, helium, argon or the like.

The reaction vessel must have stirring capabilities and must have the ability to handle subsurface inert gases during the reaction sequence, and must have heating and cooling capabilities. Further, adequate venting capabilities must be built into the system to handle system upset from the possible decomposition of hydrogen peroxide.

The mixture is stirred and heated for at least thirty (30) minutes and must be heated to at least 45° C., with or without the use of an inert gas cover, for the duration of the reaction time.

It has been found that some of the beneficial properties of the intermediates, such as high hydroxyl number and controlled epoxide content, come from this part of the reaction sequence wherein, the materials are heated for thirty (30) minutes to one hundred sixty eight (168) hours, with stirring.

Refining the product means concentration and deodorization of the product using vacuum and sparging using a material selected from nitrogen, steam, and air at a temperature of from 90° C. to 130° C. to provide a product. It is preferred to keep the temperature closer to 90° C. in order to avert the appearance of color. The concentration and deodorization step results in lower levels of decomposition products such as aldehydes and ketones which are present in other preparation processes. It has been found that beneficial properties of the intermediates, such as low odor, low color, low water content come from this part of the concentration and deodorization step.

It should be noted by those skilled in the art that this product does not have to be neutralized at any point during or after the reaction.

The preferred range for acid in this invention is 80 to 100 percent and the preferred range for the hydrogen peroxide is from 25 to 85 percent on a weight by weight basis, it being understood that peracetic and performic acids can also be used. Peracetic or performic acids are mixtures of hydrogen peroxide and acetic acid and formic acid respectively, in aqueous solutions. Peracetic acid is a transparent, faint blue colored liquid that has a piercing odor and a pH of about 2.8.

The epoxide range for the final product is in the range of 0.0 to 4.1 w/w percent and the hydroxyl number up to about 230. Preferred for this invention is an epoxide content of 0.1 to 3.5 w/w percent. More preferred are epoxide ranges from 1.2 to 3.0 percent.

Further, it is understood that this process contemplates using the fatty acid chains cleaved from the animal and plant triglyceride backbone or the methyl esters derived from the same as starting materials. In short, all grades of unsaturated biodiesel (methyl or ethyl esters) serve as suitable starting raw material for this process and are considered to be within this scope of this invention.

What is claimed is:

1. A process for the preparation of an organic reactive intermediate said process comprising:
    A. predetermining the concentrations of aqueous hydrogen peroxide and acid to be used in the process, said acid comprising an organic acid selected from the group consisting of:
        i. acetic acid,
        ii. peracetic acid,
        iii. formic acid, and,
        iv. performic acid;
    B. combining a predetermined amount of oil comprising natural triglyceride plant oils, animal oils, or a combination of natural triglyceride plant oils and animal oils, based on the weight of the oil, with the predetermined amounts of organic acid and hydrogen peroxide in a reaction vessel to form a mixture;
    C. heating the mixture to at least 45° C. under an inert atmosphere for 30 minutes to 168 hours, with stirring;
    D. concentrating and deodorizing the product from step C. by sparging using a material selected from the group consisting of
        i. nitrogen,
        ii. steam, and,
        iii. air,
    at a temperature of 90° to 130° C. to provide a organic reactive intermediate having an acid number of 2.5 to 10 mg KOH/g.

2. A process as claimed in claim 1 wherein in step D., there is a vacuum applied.

3. A process as claimed in claim 2 wherein the vacuum is in the range of 5 inches of mercury to 29.5 inches of mercury.

4. A process as claimed in claim 1 wherein in step D. the material is steam and wherein the steam has a pressure of 10 to 50 psig.

5. A process as claimed in claim 4 wherein the steam has a pressure of 20 to 40 psig.

6. A process as claimed in claim 4 wherein the steam has a pressure of 25 to 35 psig.

7. The process as claimed in claim 1 wherein the acid further comprises a mineral acid.

8. The process as claimed in claim 7 wherein the mineral acid is sulfuric acid.

9. The process as claimed in claim 1, wherein, the molar ratio of hydrogen peroxide to oil is from about 1/1 to 8/1.

10. The process as claimed in claim 1 wherein the molar ratio of acid to oil is from about 1/1 to 5/1.

11. A organic reactive intermediate prepared by the process of claim 1 wherein the organic reactive intermediate has 0.1 weight percent water or less, an acid number of 2.5 to 10 mg KOH/g and a hydroxyl number of up to about 230.

12. The process of claim 1 wherein the aqueous hydrogen peroxide is in the range of 25 to 85 percent w/w and the organic acid is in the range of 80 to 100 percent w/w pure.

13. The process of claim 1 wherein the acid is acetic acid.

14. The process of claim 1 wherein the acid is formic acid.

15. A process as claimed in claim 1 wherein the organic reactive intermediate has a hydroxyl number of up to about 230.

16. The process of claim 1 wherein the addition of oil is followed by the simultaneous addition of acid and hydrogen peroxide.

17. The process of claim 1 wherein the addition of oil is followed by acid and then hydrogen peroxide.

18. The process of claim 1 wherein the organic reactive intermediate has a biobased content of more than 90 percent by weight.

19. A process for the preparation of an organic reactive intermediate said process comprising:
    A. predetermining the concentrations of aqueous hydrogen peroxide and acid to be used in the process said acid comprising an organic acid being selected from the group consisting of
        i. acetic acid, and,
        ii. formic acid;
    B. combining a predetermined amount of oil derived materials that are by-products of the manufacture of biodiesel comprising
        i fatty acid chains cleaved from animal triglyceride backbone,
        ii plant triglyceride backbone,
        iii methyl esters derived from fatty acid chains cleaved from animal triglyceride backbone, iv methyl esters derived from fatty acid chains cleaved from plant triglyceride backbone,
v or combinations thereof;
based on the weight of the oil derived materials, with the predetermined amounts of the acid and hydrogen peroxide in a reaction vessel to form a mixture;
C. heating the mixture to at least 45° C. under an inert atmosphere for a period of time from 30 minutes to 168 hours, with stirring;
D. concentrating and deodorizing the product from step C. by sparging using a material selected from the group consisting of
i. nitrogen,
ii. steam, and,
iii. air,
at a temperature of 90° to 130° C. to provide a organic reactive intermediate having an acid number of up to about 10 mg KOH/g.

20. A product prepared by the process of claim 19 wherein the intermediate has 0.1 weight percent water or less, an acid number of up to about 10 mg KOH/g and a hydroxyl number of up to about 230.

21. The product of claim 11 wherein the product has a Gardner Color number of 7 or less.

22. The product of claim 20 wherein the product has a Gardner Color number of 7 or less.

* * * * *